United States Patent
Urbanik et al.

(10) Patent No.: US 12,337,060 B2
(45) Date of Patent: Jun. 24, 2025

(54) FERMENT FROM STRUCTURED WATER MEDIUM AND COSMETIC COMPOSITION COMPRISING THE SAME

(71) Applicant: ELC Management LLC, Melville, NY (US)

(72) Inventors: Joanna Urbanik, Westbury, NY (US); Amber Marie Nowicki, New York, NY (US); Peter John Tsolis, South Huntington, NY (US); Thomas Mammone, Farmingdale, NY (US)

(73) Assignee: ELC MANAGEMENT LLC, Melville, NY (US)

( * ) Notice: Subject to any disclaimer, the term of this patent is extended or adjusted under 35 U.S.C. 154(b) by 119 days.

(21) Appl. No.: 17/545,911

(22) Filed: Dec. 8, 2021

(65) Prior Publication Data

US 2022/0175659 A1    Jun. 9, 2022

Related U.S. Application Data

(60) Provisional application No. 63/123,441, filed on Dec. 9, 2020.

(51) Int. Cl.
| | | |
|---|---|---|
| *A61K 8/60* | (2006.01) | |
| *A61K 8/9794* | (2017.01) | |
| *A61K 8/99* | (2017.01) | |
| *A61Q 19/08* | (2006.01) | |
| *A61Q 19/00* | (2006.01) | |
| *A61Q 19/02* | (2006.01) | |

(52) U.S. Cl.
CPC ............... *A61K 8/99* (2013.01); *A61K 8/60* (2013.01); *A61K 8/9794* (2017.08); *A61Q 19/08* (2013.01); *A61Q 19/007* (2013.01); *A61Q 19/02* (2013.01)

(58) Field of Classification Search
None
See application file for complete search history.

(56) References Cited

U.S. PATENT DOCUMENTS

| | | |
|---|---|---|
| 6,135,630 A | 10/2000 | O'Neill |
| 6,139,855 A | 10/2000 | Cioca et al. |
| 6,451,328 B1 | 9/2002 | Ionita-Manzatu et al. |
| 6,905,523 B2 | 6/2005 | Vainshelboim et al. |
| 2006/0003017 A1* | 1/2006 | Ionita-Manzatu et al. ........... A61K 33/00 424/752 |
| 2006/0275351 A1 | 12/2006 | Mohammadi et al. |
| 2007/0187327 A1* | 8/2007 | George ............... A61Q 19/00 423/580.1 |
| 2010/0285176 A1* | 11/2010 | Baek ............... A23L 33/105 426/49 |
| 2012/0328597 A1 | 12/2012 | Cheng et al. |
| 2016/0361416 A1* | 12/2016 | Taylor ............... A61K 33/00 |
| 2017/0143621 A1* | 5/2017 | Baum ............... A61K 8/342 |
| 2017/0368109 A1* | 12/2017 | Petrucci ............... A61K 47/16 |
| 2019/0343746 A1* | 11/2019 | Yang ............... A61K 8/44 |
| 2021/0093539 A1* | 4/2021 | LaRosa ............... A61K 8/416 |

FOREIGN PATENT DOCUMENTS

| | | | |
|---|---|---|---|
| CN | 1371617 A | 10/2002 | |
| JP | 2003-252719 A | 9/2003 | |
| JP | 2004196664 | 7/2004 | |
| JP | 2006503804 | 2/2006 | |
| KR | 10-2019-0079514 A | 7/2019 | |
| KR | 20190079514 A * | 7/2019 | ........... A61K 8/9794 |
| WO | WO2003/092711 A1 | 11/2003 | |

OTHER PUBLICATIONS

Jiang et al., Mediators Inflamm., (2016) (Year: 2016).*
Ramachandra et al., Am. J. Agri. Biol. Sci., 3(2):502-510 (2008) (Year: 2008).*
Ro et al., Evidence-Based Complementary Alt. Medic., (2020) (Year: 2020).*
Izawa et al., H. Anazawa and S. Shimizu (eds.), Microbial Production: From Genome Design to Cell Engineering, c. 20, p. 233-242 (2014) (Year: 2014).*
Taiwan IPO Search Report from TW Application No. 110146164; Date: Aug. 9, 2022.
PCT International Search Report; International Application No. PCT/US2021/062480; Completion Date: Apr. 1, 2022; Mailing Date: Apr. 4, 2022.
PCT Written Opinion of the International Searching Authority: International Application No. PCT/US2021/062480; Completion Date: Apr. 1, 2022; Mailing Date: Apr. 4, 2022.
Supplementary European Search Report; EP Application No. 21904353.6; Completion Date: Apr. 5, 2024.

* cited by examiner

*Primary Examiner* — Michelle F. Paguio Frising
(74) *Attorney, Agent, or Firm* — Halle D. Murray

(57) ABSTRACT

A cosmetic composition comprising a ferment from a fermentation mixture comprising at least one prebiotic active ingredient, a structured water component, and at least one probiotic microorganism is disclosed. The ferment may further comprise at least one cosmetic active ingredient. A method of increasing collagen production of the skin by applying the cosmetic composition is also disclosed.

19 Claims, No Drawings

FERMENT FROM STRUCTURED WATER MEDIUM AND COSMETIC COMPOSITION COMPRISING THE SAME

CROSS-REFERENCE TO RELATED PATENT APPLICATION

This application claims the benefit of priority from U.S. Provisional Patent Application No. 63/123,441, filed Dec. 9, 2020, which is incorporated herein by reference in its entirety.

FIELD

The present disclosure relates to ferments from a fermentation mixture comprising at least one prebiotic cosmetic ingredient, a structured water component, and at least one probiotic microorganism. The ferments may further comprise at least one cosmetic active ingredient. The present disclosure also relates to cosmetic compositions comprising the ferments.

BACKGROUND

Collagen, a component of the extracellular matrix, is a major substrate protein produced by skin fibroblasts. It is an important protein, accounting for about 30% of the total weight of biological proteins and has a solid triple helix structure. Collagen forms most of the organic matter in the skin, tendons, bones and teeth, especially in bones and skin (dermis). Most other sieve structures exist as fibrous inclusions. The main function of collagen is aiding mechanical firmness of skin. However, collagen is reduced by age and photoaging by ultraviolet irradiation, which is known to be closely associated with wrinkle formation of the skin. Collagen also plays an important role in wound healing by recovering the damaged epithelium, allowing the wound to recover quickly and without scars. Furthermore, collagen possesses great tensile strength, and functions in a manner different from many other types of proteins. Collagen is found both inside and outside of cells. Collagen fibers are important in contributing to the external structure of cells and it provides firmness and strength to the skin. As people age, however, collagen degradation occurs and collagen production decreases, leading to wrinkles. As such, collagen is important for wrinkle reduction and for the reduction of visible effects of aging on the skin.

Conventionally, in order to take advantage of collagen's effect on the skin, products containing collagen in an external cosmetic composition are utilized. However, such products when applied to the skin surface are difficult to absorb through the skin and they fail to achieve that percutaneous effect. Also, such products have limited usage due to problems such as irritation and redness, or the cosmetic effects are insignificant, and thus the effect of improving skin function is unavailable as expected. Therefore, there is an urgent need for the development of a novel cosmetic composition that is more effective than existing compositions and that can promote collagen production.

Fermentation is a process of decomposing organic matter using enzymes of microorganisms. Fermenting using microorganisms reduces the toxicity levels, lowers the molecular weight, or facilitates transdermal absorption, thereby improving bioavailability. In addition, ferments exhibit effects by themselves that are enhanced through fermentation, thereby exerting effects that were not found prior to fermentation.

The disclosure is directed to a novel ferment that is unexpectedly effective in antioxidant capacities, wrinkle improvement, skin lightening, skin brightening and collagen production. The disclosure is also directed to cosmetic compositions comprising the ferment.

SUMMARY

A ferment from a fermentation mixture comprising at least one prebiotic cosmetic ingredient, a structured water component, and at least one probiotic microorganism is provided. The ferment may further comprise at least one cosmetic active ingredient.

The at least one prebiotic active ingredient may be selected from the group consisting of aloe, mango, aronia berry, raspberry, spinach, cherry broccoli, tart cherry, apple, mushroom, grape juice, beet, blueberry, blackberry, acai, coffee, ginger, cranberry, raspberry, aloe gel, coconut water, pomegranate, mango, apricot, retinol, raspberry, lavender, honey, cardamom, truffle, hyaluronic acid, and mixtures thereof. The preferred at least one prebiotic active ingredient may comprise aloe, grape juice, beet, retinol, lavender, honey, and hyaluronic acid. The more preferred at least one prebiotic active ingredient may comprise aloe and hyaluronic acid. The most preferred at least one prebiotic active ingredient may comprise aloe.

The preferred aloe may comprise Aloe Barbadensis Leaf powder. The Aloe Barbadensis Leaf powder may be present in an amount from about 0.001% to about 20% by weight, relative to the total weight of the fermentation mixture.

The fermentation mixture may further comprise hyaluronic acid. The combined amount of the Aloe Barbadensis Leaf powder and the hyaluronic acid may be from about 0.0001% to about 30% by weight, relative to the total weight of the fermentation mixture.

The structured water component may comprise I water and S water.

The at least one probiotic microorganism may be a strain selected from the group consisting of *Bifidobacterium* genus, *Lactobacillus* genus, *Enterococcus* genus, *Streptococcus* genus, *Staphylococcus* genus, *Streptococcus*, *Saccharomyces cerevisiae*, *Saccharomyces boulardii*, and mixtures thereof. The preferred at least one probiotic microorganism may be a strain selected from the group consisting of *Bifidobacterium* genus and *Lactobacillus* genus. The more preferred at least one probiotic microorganism may be *Lactobacillus* genus.

The ferment may further comprise at least one cosmetic active ingredient. The at least one cosmetic active ingredient may be selected from the group consisting of Aloe Barbadensis Leaf Polysaccharides, mango, aronia berry, raspberry, spinach, cherry broccoli, tart cherry, apple, mushroom, grape juice, beet, blueberry, blackberry, acai, coffee, ginger, cranberry, raspberry, aloe gel, coconut water, pomegranate, mango, apricot, retinol, raspberry, lavender, honey, cardamom, truffle, hyaluronic acid, and mixtures thereof. The preferred at least one cosmetic active ingredient may comprise Aloe Barbadensis Leaf Polysaccharides, grape juice, beet, retinol, lavender, honey, and hyaluronic acid. The more preferred at least one cosmetic active ingredient may comprise Aloe Barbadensis Leaf Polysaccharides and hyaluronic acid. The most preferred at least one cosmetic active ingredient may comprise Aloe Barbadensis Leaf Polysaccharides.

The ferment may comprise structured water. The structured water component may be present in the ferment from about 1% to about 99.5% by weight, relative to the total weight of the ferment. The I water may be present in an amount from about 1% to about 60% by weight of the ferment. The S water may be present in an amount from about 1% to about 60% by weight of the ferment.

The ferment may be in a form of an extract, lysate, or filtrate.

A cosmetic composition comprising a ferment from the fermentation mixture comprising at least one prebiotic cosmetic ingredient, a structured water component, and at least one probiotic microorganism is also provided. The ferment may be present from about 0.0001% to about 30% by weight, relative to the total weight of the cosmetic composition.

The cosmetic composition is a skin lotion, skin softener, skin toner, astringent, lotion, milk lotion, moisturizing lotion, nutrition lotion, massage cream, facial mask, facial cleanser, nutrition cream, moisturizing cream, hand cream, foundation, essence, nutrition essence, cleansing foam, cleansing lotion, cleansing cream, body lotion, body mask, or body cleanser.

A method of increasing collagen production in the human skin is provided. The method comprising the step of applying a cosmetic composition comprising a fermentation extract from a fermentation mixture comprising at least one probiotic microorganism, a prebiotic active ingredient and a structured water component. The most preferred prebiotic active ingredient may comprise Aloe Barbadensis Leaf powder. The structured water component may comprise I water and S water. The composition may be applied topically, once, twice or thrice a day or prior to retiring to bed at night. The composition may enhance hydration and moisturization of the skin for up to 100 hours and provides skin brightening and skin lightening effect on the skin upon topical application.

DETAILED DESCRIPTION

The dimensions and values disclosed herein are not to be understood as being strictly limited to the exact numerical values recited. Instead, unless otherwise specified, each such dimension is intended to mean both the recited value and a functionally equivalent range surrounding that value. Except in operating and comparative examples, or where otherwise explicitly indicated, all numbers in this description indicating amounts or ratios of material or conditions of reaction, physical properties of materials and/or use are to be understood as modified by the word "about". All amounts are by weight of the final composition, unless otherwise specified.

The terms "active ingredient" or "active agent" or "cosmetic agent" means a cosmetic agent that is utilized to deliver a benefit to the skin. An "active ingredient" or "active agent" or "cosmetic agent" would cause a change in the subject's skin or deliver the benefits under consideration, and thus, aid in accomplishing a desired, expected, or an intended result. The terms "active ingredient" or "active agent" or "cosmetic agent" according to the present invention include cosmetically acceptable excipients or carriers that may be present in a composition/formulation.

The terms "prevent" and "preventing" include the prevention of the recurrence, spread or onset of a skin or hair condition. It is not intended that the present invention be limited to complete prevention.

The term "subject" refers to any mammal, preferably a human.

The term "topical" refers to administration of an agent or agents (e.g., cosmetic, vitamin, etc.) on the skin.

The terms "transdermal" or "topical" refers to the delivery of an agent (e.g., cosmetic, dermatological, vitamin, etc.) through the skin (e.g., so that at least some portion of the population of particles reaches underlying layers of the skin).

The terms "inhibiting," "reducing," or "prevention," or any variation of these terms, when used in the claims and/or the specification includes any measurable decrease or complete inhibition to achieve a desired result.

The term "effective," as that term is used in the specification and/or claims, means adequate to accomplish a desired, expected, or intended result.

The term "structured water," as used in the specification and/or claims, means water that contains stabilized clusters of ions, which is disclosed in U.S. Pat. Nos. 6,139,855; 6,1356,30; 6,451,328; 6,905,523 and in U.S. patent applications Ser. Nos.: 02/12,326; 11/673,119 and 11/421,834, the entire disclosures of which are hereby incorporated by reference herein.

The term "I water," as used in the specification and/or claims, means acid fraction of the structured water, which is disclosed in U.S. Pat. Nos. 6,139,855; 6,1356,30; 6,451,328; 6,905,523 and in U.S. patent applications Ser. Nos.: 02/12,326; 11/673,119 and 11/421,834, the entire disclosures of which are hereby incorporated by reference herein.

The term "S water," as used in the specification and/or claims, means basic fraction of the structured water, which is disclosed in U.S. Pat. Nos. 6,139,855; 6,1356,30; 6,451,328; 6,905,523 and in U.S. patent applications Ser. Nos.: 02/12,326; 11/673,119 and 11/421,834, the entire disclosures of which are hereby incorporated by reference herein.

The ferment may be produced from a fermentation mixture comprising at least one prebiotic cosmetic ingredient, a structured water component, and at least one probiotic microorganism. Accordingly, the applicants were able to achieve a novel ferment by utilizing the structured water component in the fermentation mixture.

The at least one prebiotic cosmetic ingredient may be selected from a group consisting of aloe, aronia berry, raspberry, spinach, cherry broccoli, tart cherry, apple, mushroom, grape juice, beet, blueberry, blackberry, acai, coffee, ginger, cranberry, raspberry, coconut water, pomegranate, mango, apricot, retinol powder, raspberry powder, lavender, honey, cardamom, truffle, hyaluronic acid or mixtures thereof. The preferred at least one prebiotic cosmetic ingredient may be from aloe. The more preferred at least one prebiotic cosmetic ingredient may be from Aloe barbadensis Miller.

When the at least one prebiotic cosmetic ingredient is from plants, the relevant plant part may be leaf, stem, flower, root, seed, fruit, tuber, or coleoptile. The preferred plant part may be leaf, stem, flower, or fruit. The more preferred plant part may be leaf.

The at least one prebiotic cosmetic ingredient may be present in a form of powder, liquid, semi-aqueous liquid, or concentrated form. The preferred form is the powder.

The most preferred prebiotic cosmetic ingredient is Aloe Barbadensis Leaf Powder.

The prebiotic cosmetic ingredient may be present in the fermentation mixture in an amount ranging from about 0.00001% to about 20%, preferably from about 0.0001% to about 10%, more preferably from about 0.001% to about 5%, and most preferably from about 0.01% to about 3%, with all percentages mentioned herein by weight, relative to the total weight of the fermentation mixture.

Aloe Barbadensis Leaf Powder may be produced by processing Aloe Barbadensis Miller leaves within 4 hours since the time of harvesting. The inner fillet of the aloe is extracted, the fiber is removed, while the aloin is removed by charcoal absorption, filtered, pasteurized and concentrated. The concentrate is then spray dried to a powder form with less than 7% moisture content. The powder is free of preservatives or matrix and includes at least 10% polysaccharides (such as, without limitation, starch, cellulose, glycogen, peptidoglycan and the like).

The structured water component is described in U.S. Pat. Nos. 6,139,855; 6,135,630; 6,451,328; 6,905,523 and in U.S. patent applications Ser. Nos.: US02/12326; 11/673,119 and 11/421,834, all of which are incorporated herein in their entireties. The structured water component may comprise I water and S water.

The structured water is defined as water that contains stabilized clusters of ions. The structured water I (or "I water") is the acid fraction that contains stabilized clusters of R+ (H)– (Cl–, PO4 3–, SO4 2–) ions. The structured water S (or "S water") is the basic fraction that contains stabilized clusters of R+(OH)-n (Ca2+, Mg2+, Na+, K+, etc.) ions. Preferably, I water is characterized by a conductivity of about 500-3000 μS and pH of about 2.0-3.0; and S water is characterized by a conductivity of about 600-2500 μS, and a pH of about 10-12, each resulting from starting water with μS/cm of about 250-450, and a pH of about 7-7.5.

The structured water component may be present in the fermentation mixture in an amount ranging from about 80% to about 99.999%, preferably from about 90% to about 99.99%, more preferably from about 95% to about 99.9%, most preferably form about 98% to about 99% with all percentages mentioned herein by weight, relative to the total weight of the fermentation mixture.

It is most unexpected that surprising advantageous efficacies can be achieved by using structured water in fermentation medium.

It was also unexpected that the advantageous efficacies of the ferment do not come from structured water ending up with the final ferment.

The probiotic microorganism(s) may be included in the form of fractions of cell components. The probiotic microorganism(s) or fraction(s) may also be introduced in the ferment in the form of a freeze-dried powder, a culture supernatant and/or, where appropriate, in a concentrated form.

The at least one probiotic microorganism may be selected from a group consisting of Ascomycetes such as *Bifidobacterium, Yarrowia, Kluyveromyces, Torulaspora, Schizosaccharomyces pombe, Debaromyces, Candida, Pichia, Aspergillus* and *Penicillium*, bacteria of the genera *Bifidobacterium, Bacteroides, Fusobacterium, Melissococcus, Propionibacterium, Enterococcus, Lactococcus, Staphylococcus, Peptostrepococcus, Bacillus, Pediococcus, Micrococcus, Leuconostoc, Weissella, Aerococcus, Oenococcus* and *Lactobacillus*, or mixtures thereof.

The probiotic microorganism may also include, without limitation, both bacterial and yeast genera such as lactic acid bacteria, that produce lactic acid by fermentation of sugar, *Lactobacillus* species such as *Lactobacillus acidophilus, amylovorus, casei, rhamnosus, brevis, crispatus, delbrueckii* (subsp. *bulgaricus, lactis*), *fermentum, helveticus, gallinarum, gasseri johnsonii, paracasei, plantarum, reuteri, salivarius, alimentarius, curvatus, casei* (subsp. *casei, sake*), *Gocci* species including, *Lactococcus lactis* (subsp. *lactis* or *cremoris*), *Leuconstoc mesenteroides* (subsp. *Dextranicum*); *Pediococcus acidilactici, Sporolactobacillus inulinus, Streptococcus salvarius* (subsp. *Thermophilus*), *Streptococcus thermophilus, Staphylocccus carnosus, Staphylococcus xylosus, Bifidobacteria* or *Bifidobacterium* species including, *Bifidobacterium adolescentis, animalis, bifidum, breve, lactis, longum, infantis, pseudocatenulatum*, yeasts such as *Saccharomyces* (*cerevisiae* or *boulardii*), or other sporulating bacteria such as *Bacillus* (*cereus var toyo* or *subtilis*), *Bacillus coagulans, Bacillus licheniformis, Escherichia coli* strain nissle, *Propionibacterium freudenreichii*, or mixtures thereof.

The preferred at least one probiotic microorganism may be a strain selected from the group consisting of *Bifidobacterium* genus and *Lactobacillus* genus. The more preferred at least one probiotic microorganism may be from *Lactobacillus* genus.

Examples of the *Lactobacillus* genus include, without limitation, *Lactobacillus, Lactobacillus acidophilus, Lactobacillus amylovorus, Lactobacillus casei, Lactobacillus rhamnosus, Lactobacillus brevis, Lactobacillus crispatus, Lactobacillus delbrueckii, Lactobacillus fermentum, Lactobacillus helveticus, Lactobacillus gallinarum, Lactobacillus gasseri, Lactobacillus johnsonii, Lactobacillus paracasei, Lactobacillus plantarum, Lactobacillus reuteri, Lactobacillus salivarius, Lactobacillus alimentarius, Lactobacillus curvatus, Lactobacillus casei, Lactobacillus sake, Lactococcus lactis, Lactococcus lactis, Leuconstoc mesenteroides, Pediococcus acidilactici, Sporolactobacillus inulinus, Streptococcus salvarius, Streptococcus thermophilus, Staphylocccus carnosus, Staphylococcus xylosus, Saccharomyces* (*cerevisiae* or *boulardii*), *Bacillus* (*cereus var toyo* or *subtilis*), *Bacillus coagulans, Bacillus licheniformis, Escherichia coli, Propionibacterium freudenreichii*, or mixtures thereof. The preferred species are *Lactobacillus johnsonii, Lactobacillus paracasei, Bifidobacterium adolescentis, Bifidobacterium longum* and *Bifidobacterium lactis*, or mixtures thereof.

Examples of *Bifidobacterium* genus include, but is not limited to, *adolescentis, longum* and *lactis*.

The probiotic microorganism may be present in the fermentation mixture in an amount ranging from about 0.001% to about 5%, preferably from about 0.005% to about 1%, more preferably from about 0.01% to about 0.5%, most preferably form about 0.05% to about 0.15% with all percentages mentioned herein by weight, relative to the total weight of the fermentation mixture.

The ferment may further comprise at least one cosmetic active ingredient. The at least one cosmetic active ingredient may be selected from the group consisting of Aloe Barbadensis Leaf Polysaccharides, mango, aronia berry, raspberry, spinach, cherry broccoli, tart cherry, apple, mushroom, grape juice, beet, blueberry, blackberry, acai, coffee, ginger, cranberry, raspberry, aloe gel, coconut water, pomegranate, mango, apricot, retinol, raspberry, lavender, honey, cardamom, truffle, hyaluronic acid, and mixtures thereof. The preferred at least one cosmetic active ingredient may comprise Aloe Barbadensis Leaf Polysaccharides, grape juice, beet, retinol, lavender, honey, and hyaluronic acid. The more preferred at least one cosmetic active ingredient may comprise Aloe Barbadensis Leaf Polysaccharides and hyaluronic acid. The most preferred at least one cosmetic active ingredient is Aloe Barbadensis Leaf Polysaccharides.

Nonlimiting examples of suitable Aloe Barbadensis Leaf Polysaccharides include the commercially available ingredient under the trade name ALOE VERA IL SD PWD 200X 705AV ORGANIC from Ashland Inc.

The cosmetic active ingredient may be present in the ferment in an amount ranging from about 0.000001% to about 10%, preferably from about 0.00001% to about 1%, more preferably from about 0.00005% to about 0.1%, and most preferably from about 0.0001% to about 0.01%, with all percentages mentioned herein by weight, relative to the total weight of the ferment.

The at least one cosmetic active ingredient may be introduced into the ferment in the form of a cosmetic active ingredient solution in structured water. The cosmetic active ingredient may be present in the structured water solution in an amount ranging from about 0.0001% to about 20%, preferably from about 0.001% to about 10%, more preferably from about 0.005% to about 1%, and most preferably from about 0.01% to about 0.1%, with all percentages mentioned herein by weight, relative to the total weight of the cosmetic active ingredient solution in structured water.

The ferment may be in the form of a lysate, extract, filtrate, or both. In the case of a lysate, the fermentation product is lysed. In the case of a filtrate or extract, the fermentation product is filtered. The preferred form of the ferment is filtrate.

The method of producing the ferment may comprise following steps: 1) making a fermentation mixture by mixing at least one prebiotic cosmetic ingredient, a structured water component, and at least one probiotic microorganism; 2) stirring the fermentation mixture at the temperature of between 20° C. and 30° C., preferably at about 25° C., for the period of between 1 to 10 days, preferably between 2 to 8 days, more preferably between 3 and 5 day; 3) increasing the temperature to between 40° C. and 50° C., preferably to about 45° C., and maintaining that temperature for the period of 12 hours to 36 hours, preferably for about 24 hours; 4) filtering the resulted mixture of step 3); 5) optionally, adding the structured water solution or suspension of at least one cosmetic active ingredient into the filtrate resulted in step 4), wherein the structured water solution or suspension of at least one cosmetic active ingredient comprises the at least one cosmetic active ingredient in an amount ranging from about 0.0001% to about 20%, preferably from about 0.001% to about 10%, more preferably from about 0.005% to about 1%, and most preferably from about 0.01% to about 0.1%, (w/w), relative to the total weight of the structured water solution or suspension. Preferably, the method of producing the ferment comprises the step 5). More preferably, the structured water solution or suspension of at least one cosmetic active ingredient is a solution.

In the optional step 5) of the method of producing the ferment, the addition amount of the structured water solution of at least one cosmetic active ingredient may range from about 0.01% to about 20%, preferably from about 0.1% to 10%, more preferably from about 0.5% to 8%, most preferably from about 1% to about 5% (w/w), relative to the total weight of the fermentation mixture of the step 1).

A cosmetic composition comprising the ferment is also provided herein. The ferment is produced from a fermentation mixture comprising at least one prebiotic cosmetic ingredient, a structured water component, and at least one probiotic microorganism, wherein the structured water component comprises I water and S water. Preferably, the ferment may further comprise at least on cosmetic active ingredient.

Specifically, the cosmetic compositions provide improved penetration of the cosmetic ingredients into the layers of the skin, enhances hydration of the skin, provides skin whitening and brightening benefit, improves the integrity of the skin and improves bioavailability of the cosmetic product.

The cosmetic composition may comprise the ferment in an amount ranging from about 0.00001% to about 20%, preferably from about 0.0001% to about 15%, more preferably from about 0.001% to about 10%, most preferably from about 0.001% to about 5% (w/w), relative to the total weight of the composition.

The cosmetic composition may comprise at least one cosmetic active ingredients in an amount ranging from about 0.0001% to about 20% by weight, relative to the total weight of the ferment. In yet other compositions, the ferment comprising the prebiotic may be formulated to include other cosmetically active ingredients such as, for example, hyaluronic acid in effective amounts. In such compositions, the combined amount of the prebiotic cosmetic ingredient and other cosmetic ingredient, such as, without limitation, hyaluronic acid ranges from about 0.00001% to about 30% by weight, relative to the total weight of the composition. Further, such compositions may include a combination of cosmetic ingredients in an amount ranging from about 0.0001% to about 20% by weight, relative to the total weight of the composition.

The cosmetic compositions can be used in any topically applied skin care product with an aqueous media component. For example, the structured water can be employed in a purely aqueous culture media, a hydroalcoholic media, or as part of the aqueous phase of a water-in-oil or oil-in-water emulsion. The composition may include a vehicle suitable for topical application to the skin, such as, for example, solutions, colloidal dispersions, emulsions, suspensions, creams, lotions, gels, foams, mousses, sprays and the like. The type of cosmetic active and the activity that is enhanced by the presence of I and S water, can be any which is beneficially used in a skin care product. For example, the structured water is useful in enhancing the moisturization properties of a fermentation extract comprising moisturizing actives. The fermentation extract can also be used to enhance the activity of agents or cosmetic actives used to treat age spots, keratoses and wrinkles, as well as analgesics, anesthetics, anti-acne agents, antibacterials, antiyeast agents, antifungal agents, antioxidants, antiviral agents, antidandruff agents, antidermatitis agents, antipruritic agents, antiemetics, antimotion sickness agents, anti-irritant agents, anti-inflammatory agents, antihyperkeratolytic agents, antidry skin agents, antiperspirants, antipsoriatic agents, antiseborrheic agents, hair conditioners and hair treatment agents, antiaging agents, antiwrinkle agents, sunscreen agents, antihistamine agents, skin lightening agents, depigmenting agents, wound-healing agents, vitamins, corticosteroids, self-tanning agents, or hormones. All such benefit enhancing cosmetic actives are contemplated to be utilized along with the structured water described herein, as the fermentation media and therefore, is contemplated to be within the disclosure.

The I/S water media can be used in an amount from about 1% to about 99.5% by weight of the ferment as a whole, but more frequently will be used at levels of from about 20-80%, from about 40 to about 80%. The ferment comprising I/S water itself can constitute the entire aqueous component of the composition. Alternately, the I and S combination can be a portion of the aqueous component of the fermented media, i.e., further combined with other non-structured aqueous components, such as distilled water, or a floral water. The use of non-structured water with structured water in the fermented media is possible, since the enhancing effect of the I/S combination has been observed even at dilutions of ¹⁄₁₀₀₀.

The structured water is the media of the ferment and may be additionally present in the composition. In addition to the I water and S water, the structured water further includes salts. Such salts provide salinity, osmolarity or osmolality to the fermentation media. The combination of I water and S water, at a specific ratio/amounts and the salts, creates a unique environment within the fermentation media for the microorganism to survive and thrive. As a result, the microorganism is capable of metabolizing the prebiotic active ingredient present in the media effectively, thereby, creating a unique postbiotic ferment that includes multiple metabolites or intermediates that are efficacious. Such metabolites and any intermediate fermentation products are contemplated to be within the disclosure.

The ferment can be used in any type of skin care or makeup product that has an aqueous component. For example, it can be used to enhance the properties of actives used in makeup products, such as lipsticks and glosses, foundations, primers, blushes, eyeliners, eyeshadows and the like. It will also be useful in treatment products, in which the efficacy of active components is particularly desired.

Accordingly, the ferment described herein is produced from a fermentation mixture comprising at least one prebiotic cosmetic ingredient, a structured water component, and at least one probiotic microorganism. Optionally, the ferment may include any cosmetically acceptable excipients. The ferment provide a unique postbiotic blend that exhibits increased bioavailability, penetration and efficacy on the human skin. The cosmetic compositions comprising such ferment are utilized for external topical administration and, which may be aqueous, aqueous-alcoholic or oily solutions, dispersions of the solution type or dispersions of the lotion or serum type, emulsions of liquid or semi-liquid consistency of the milk type, suspensions or emulsions of the cream type, aqueous or anhydrous gels, microemulsions, microcapsules, microparticles, or vesicular dispersions of ionic and/or nonionic type.

Accordingly, the applicants developed cosmetic compositions or products comprising the novel ferment. Such compositions have shown to provide efficacious collagen production activity, anti-aging activity without cytotoxicity, skin lightening and brightening effects. Specifically, the compositions comprising the ferment overcomes the issues with bioavailability of the active, allowing for maximum efficacy on the skin. This novel ferment has shown to increase collagen production, in vitro by about 48%. Further, the composition comprising the ferment is also shown to provide supercharged hydration, penetrating multiple layers deep into the skin surface. The composition also activates skin's own moisture reservoirs for hydration lasting up to 100 hours to maximize hydration.

The methods of use for the compositions will depend on the ultimate intended use of composition. For example, the compositions described herein may be applied to the skin regularly at night and during the day. The composition may also be applied to the skin in a regular manner once, twice or thrice a day from about one to eight weeks or as many weeks as required or desired.

Additional Components

The compositions herein may further contain other additional components, which may be selected by the artisan according to the desired characteristics of the final product and which are suitable for rendering the compositions more cosmetically or aesthetically acceptable or to provide them with additional usage benefits. The components useful herein are conveniently categorized by a certain benefit or their postulated mode of action, however, a given category is not limiting of its use. Further, it is understood that one component may provide multiple benefits.

The CTFA Cosmetic Ingredient Handbook, Tenth Edition (published by the Cosmetic, Toiletry, and Fragrance Association, Inc., Washington, D.C.) (2004) (hereinafter "CTFA"), describes a wide variety of non-limiting materials that can be added to a composition herein. Examples of these ingredient classes include, but are not limited to: abrasives, absorbents, aesthetic components such as fragrances, pigments, colorings/colorants, essential oils, skin sensates, astringents, such as cosmetic and drug astringents (e.g., clove oil, menthol, camphor, *eucalyptus* oil, eugenol, menthyl lactate, witch hazel distillate), anti-acne agents, anti-caking agents, antifoaming agents, antimicrobial agents (e.g., iodopropnyl butylcarbamate), antibacterial agents, antifungal agents, antioxidants, binders, biological additives, buffering agents, bulking agents, chelating agents, chemical additives, colorants, cosmetic biocides, denaturants, external analgesics, film formers or materials, e.g., polymers, for aiding the film-forming properties and substantivity of the composition (e.g., copolymer of eicosene and vinyl pyrrolidone), opacifying agents, pH adjusters, plant derivatives, plant extracts, plant tissue extracts, plant seed extracts, plant oils, preservatives, propellants, reducing agents, sebum control agents, and sequestrants. Other optional components which may be incorporated in a composition described herein include, but are not limited to, one or more cosmetic skin care agents. A cosmetic skin care agent is any substance, material, or compound, intended to be applied to the skin for the purpose of improving an undesirable skin condition (or symptom thereof). Some undesirable skin conditions include outward visibly and tactilely perceptible manifestations as well as any other macro or micro effects due to skin aging. Such signs may be induced or caused by intrinsic factors or extrinsic factors, e.g., chronological aging and/or environmental damage. These signs may result from processes which include, but are not limited to, the development of textural discontinuities such as wrinkles, including both fine superficial wrinkles and coarse deep wrinkles, folds, skin lines, crevices, bumps, large pores (e.g., associated with adnexal structures such as sweat gland ducts, sebaceous glands, or hair follicles), scaliness, flakiness and/or other forms of skin unevenness or roughness, loss of skin elasticity (loss and/or inactivation of functional skin elastin), sagging (including puffiness in the eye area and jowls), loss of skin firmness, loss of skin tightness, loss of skin recoil from deformation, discoloration (including undereye circles), blotching, sallowness, hyperpigmented skin regions such as age spots and freckles, keratoses, abnormal differentiation, hyperkeratinization, elastosis, collagen breakdown, and other histological changes in the stratum corneum, dermis, epidermis, the skin vascular system (e.g., telangiectasia or spider vessels), and underlying tissues, especially those proximate to the skin.

The composition may comprise a dermatologically, cosmetically acceptable carrier or excipient. The carrier may thus act as a diluent, dispersant, solvent, or the like for the peptide and other materials, compounds and/or agents. Exemplary acceptable excipients include any and all solvents, dispersion media, diluents, or other liquid vehicles, dispersion or suspension aids, surface active agents, isotonic agents, thickening or emulsifying agents, preservatives, solid binders, lubricants as suited for the topical administration and dosage. Except insofar as any conventional carrier medium is incompatible with a substance or its derivatives, such as by producing any undesirable biological effect or otherwise interacting in a deleterious manner with any other component(s) of the composition, its use is contemplated to be within the scope of this invention. The carrier may contain one or more acceptable solid, semi-solid or liquid fillers, diluents, solvents, extenders and the like. The carrier may be solid, semi-solid or liquid. The carrier can itself be inert or it can possess dermatological or cosmeceutical benefits of its own. Concentrations of the carrier can vary with the carrier selected and the intended concentrations of the essential and optional components. In compositions, the carrier is present at a level of from about 50% to about 99.99% (e.g., from about 60% to about 99.9%, or from about 70% to about 98%, or from about 80% to about 95%), by weight of the composition. The acceptable carrier may be provided in a wide variety of forms. Non-limiting examples include, but are not limited to, simple solutions (water or oil-based), emulsions, and solid or semi-solid forms (gels, sticks). For example, emulsion carriers can include, but are not limited to, oil-in-water, water-in-oil, water-in-silicone, water-in-oil-in-water, and oil-in-water-in-silicone emulsions. As will be understood by the skilled artisan, a given component will distribute primarily into either the water or oil phase, depending on the water solubility/dispersibility of the component in the composition. In some embodiments, a personal care composition described herein is formulated into an oil-in-water emulsion.

Suitable carriers also include oils. The composition may comprise from about 1% to about 95% by weight of one or more oils. The composition may comprise from about 0.1%, 0.5%, 1%, 2%, 5%, 10%, 15%, 20%, 25%, 30%, 35%, 40%, 45%, 50%, 55%, 60%, 65%, 70%, 75%, 80%, 85%, or 90% to about 90%, 85%, 80%, 75%, 70%, 65%, 60%, 55%, 50%, 45%, 40%, 35%, 30%, 25%, 20%, 15%, 10%, 5%, or 3% of one or more oils. Oils may be used to solubilize, disperse, or carry materials that are not suitable for water or water-soluble solvents. Suitable oils include silicones, hydrocarbons, esters, amides, ethers, and mixtures thereof. Oils may be fluid at room temperature. The oils may be volatile or nonvolatile. "Non-volatile" means a material that exhibit a vapor pressure of no more than about 0.2 mm Hg at 25° C. at one atmosphere and/or a material that has a boiling point at one atmosphere of at least about 300° C. "Volatile" means that the material exhibits a vapor pressure of at least about 0.2 mm Hg at 20° C. Volatile oils may be used to provide a lighter feel when a heavy, greasy film is undesirable. When the skin care composition is in the form of an emulsion, oils are carriers typically associated with the oil phase. The composition may comprise an emulsifier. An emulsifier is particularly suitable when the composition is in the form of an emulsion or if immiscible materials are being combined. The skin care composition may comprise from about 0.05%, 0.1%, 0.2%, 0.3%, 0.5%, or 1% to about 20%, 10%, 5%, 3%, 2%, or 1% emulsifier. Emulsifiers may be nonionic, anionic or cationic. The compositions described herein may be in the form of pourable liquids (under ambient conditions). The compositions can therefore comprise an aqueous carrier, which is typically present at a level of from about 20% to about 95% (or from about 60% to about 85%) based on weight of the composition. The aqueous carrier may comprise water, or a miscible fermentation mixture of water and organic solvent, but preferably comprises water with minimal or no significant concentrations of organic solvent, except as otherwise incidentally incorporated into the composition as minor ingredients of other essential or optional components.

The compositions of the present invention also comprise, the carrier is present at a level of from about 20% to about 99.99%, about 30% to about 90%, about 40% to about 80% by weight of the composition. The carrier can be in a wide variety of forms. Non-limiting examples include simple solutions (e.g., aqueous, organic solvent, or oil based), emulsions, suspensions, and solid forms (e.g., gels, sticks, flowable solids, or amorphous materials). In certain embodiments, the dermatologically acceptable carrier is in the form of an emulsion or suspension. Emulsions or suspensions may be generally classified as having a continuous aqueous phase (e.g., oil-in-water and water-in-oil-in-water) or a continuous oil phase (e.g., water-in-oil and oil-in-water-in-oil). The oil phase of the present invention may comprise silicone oils, non-silicone oils such as hydrocarbon oils, esters, ethers, and the like, and mixtures thereof.

Emulsions may further comprise an emulsifier. The composition may comprise any suitable percentage of emulsifier to sufficiently emulsify the carrier. Suitable weight ranges include from about 0.1% to about 10% or about 0.2% to about 5% of an emulsifier, based on the weight of the composition. Emulsifiers may be nonionic, anionic or cationic. Suitable emulsifiers are disclosed in, for example, U.S. Pat. Nos. 3,755,560, 4,421,769, and McCutcheon's Detergents and Emulsifiers, North American Edition, pages 317-324 (1986). Suitable emulsions may have a wide range of viscosities, depending on the desired product form. The carrier may further comprise a thickening agent as are well known in the art to provide compositions having a suitable viscosity and rheological character.

Transdermal Delivery Vehicle

The transdermal delivery vehicle may comprise a physical or chemical mechanism designed to deliver materials beneath the skin's surface. Such physical mechanisms may include, for example, known penetration enhancing cosmetic compositions or ingredients, hypodermic needles, microneedles, transdermal patches, electrospun nanofibers, and the like. Other delivery systems may include, for example, using chemical enhancers, non-cavitational ultrasound, iontophoresis and other energy devices. The compositions herein may further include at least one film-forming polymer. The film-forming polymer may be chosen from cellulose polymers, such as nitrocellulose, cellulose acetate, cellulose acetate/butyrate, cellulose acetate/propionate, and ethyl cellulose; polyurethanes; acrylic polymers; vinyl polymers; polyvinylbutyrals; alkyd resins; resins resulting from aldehyde condensation products, such as arylsulphonamide-formaldehyde resins, for example, toluenesulphonamide-formaldehyde resin, and arylsulphonamide-epoxy resins. Further non-limiting examples of suitable film-forming polymers include nitrocellulose from Hercules; toluenesulphonamide-formaldehyde resins "Ketjentflex MS80" from Akzo, "Santolite MHP", "Santolite MS 80", and "Resimpol 80" from Pan Americana, the alkyd resin "Beckosol ODE 230-70-E" from Dainippon, the acrylic resin "Acryloid B66" from Rohm & Haas, and the polyurethane resin "Trixene PR 4127" from Baxenden. The film-forming polymer may generally be present at about 1% to about 50%, preferably from about 2% to about 40%, and most preferably from about 2% to about 35% of the composition.

Anti-Oxidants and Radical Scavengers

Anti-oxidants and radical scavengers are especially useful for providing protection against UV radiation which can cause increased scaling or texture changes in the stratum corneum and against other environmental agents which can cause skin damage. Such anti-oxidants/radical scavengers include, for example, tocopherol sorbate and other esters of tocopherol, and tocopherol sorbate.

Anti-Inflammatory Agents

Anti-inflammatory agents enhance the skin appearance benefits, by for example, contribution of uniformity and acceptable skin tone and/or color. Optionally, the anti-inflammatory agent includes a steroidal anti-inflammatory agent and a non-steroidal anti-inflammatory agent. The steroidal anti-inflammatory agent may be hydrocortisone. So-called "natural" anti-inflammatory agents are also useful. For example, alpha bisabolol, aloe vera, Manjistha (extracted from plants in the genus *Rubia*, particularly *Rubia Cordifolia*), and Guggal (extracted from plants in the genus *Commiphora*, particularly *Commiphora Mukul*), kola extract, chamomile, and sea whip extract, may also be used.

Antimicrobial Agents

As used herein, "antimicrobial agents" means a compound capable of destroying microbes, preventing the development of microbes or preventing the pathogenic action of microbes. Antimicrobal agents are useful, for example, in controlling acne. Preferred antimicrobial agents are benzoyl peroxide, erythromycin, tetracycline, clindamycin, azelaic acid, sulfur resorcinol, phenoxyethanol, and Irgasan™ DP 300 (Ciba Geigy Corp., U.S.A.). A safe and effective amount of an antimicrobial agent may be added to emulsions herein, preferably from 0.001% to 10%, more preferably from 0.01% to 5%, still more preferably from 0.05% to 2%.

Chelators

As used herein, "chelator" refers to a compound that reacts for removing a metal ion from a system by forming a complex so that the metal ion cannot readily participate in or catalyze chemical reactions. The inclusion of a chelator is especially useful for providing protection against UV radiation which can contribute to excessive scaling or skin texture changes and against other environmental agents which can cause skin damage. Exemplary chelators that are useful herein are disclosed in U.S. Pat. No. 5,487,884, Bissett et al, issued Jan. 30, 1996; PCT application 91/16035 and 91/16034, Bush et al, published Oct. 31, 1995. Preferred chelators are furildioxime and derivatives thereof.

Silicone Elastomers

The compositions may include a non-emulsifying cross-linked organopolysiloxane elastomer. The term "non-emulsifying", as used herein, defines crosslinked organopolysiloxane elastomers from which polyoxyalkylene units are absent. Such elastomers are used to reduce the tackiness/stickiness feel associated with skin conditioning agents.

The elastomers may be dimethicone/vinyl dimethicone crosspolymers, vinyl dimethicone/lauryl dimethicone crosspolymers, C30-C45, alkyl ceteayl dimethicone/polycyclohexane oxide crosspolymers, and mixtures thereof.

Dimethicone/vinyl dimethicone crosspolymers are supplied by a variety of suppliers including Dow Corning (DC 9040 and DC 9041), General Electric (SFE 839), Shin Etsu (KSG-15, 16, 18 [dimethicone/phenyl vinyl dimethicone crosspolymer]), and Grant Industries (GRANSIL™ line of elastomers). Cross-linked organopolysiloxane elastomers and processes for making them are further described in U.S. Pat. No. 4,970,252 to Sakuta, et al., issued Nov. 13, 1990; U.S. Pat. No. 5,760,116 to Kilgour, et al., issued Jun. 2, 1998; U.S. Pat. No. 5,654,362 to Schulz, Jr., et al. issued Aug. 5, 1997.

The vinyl dimethicone/lauryl dimethicone crosspolymers include vinyl dimethicone/lauryl dimethicone crosspolymer & mineral oil (tradename KSG-41); vinyl dimethicone/lauryl dimethicone crosspolymer & isododecane (tradename KSG-42); vinyl dimethicone/lauryl dimethicone crosspolymer & triethylhexanoin (tradename KSG-43); vinyl dimethicone/lauryl dimethicone crosspolymer & squalane (tradename KSG-44). Each of these "KSG" denominated silicone elastomers is available from Shinestu Chemical.

Commercially available cyclomethicone and C30-C45 alkyl ceteayl dimethicone/polycyclohexane oxide crosspolymer is available from GE Silicone under the tradename Velvasil 125.

Whitening Agents

The compositions herein may further comprise from 0.001% to 10%, or from 0.1% to 5% of a whitening agent. Nonlimiting examples of suitable whitening agents are those which are compatible with aqueous compositions. The whitening agents may include active ingredients that not only alter the appearance of the skin, but also improve hyperpigmentation as compared to pre-treatment.

Useful whitening agents may include ascorbic acid compounds, azelaic acid, butyl hydroxy anisole, gallic acid and its derivatives, glycyrrhizinic acid, hydroquinoine, kojic acid, arbutin, mulberry extract, and mixtures thereof. Use of combinations of whitening agents is believed to be advantageous in that they may provide whitening benefit through different mechanisms.

The ascorbic acid compound may be an ascorbic acid salt or derivative thereof. Exemplary water-soluble salt derivatives include, but are not limited to, L-ascorbic acid 2-glucoside, L-ascorbyl phosphate ester salts such as sodium L-ascorbyl phosphate, potassium L-ascorbyl phosphate, magnesium L-ascorbyl phosphate, calcium L-ascorbyl phosphate, aluminum L-ascorbyl phosphate. L-ascorbyl sulfate ester salts can also be used. Examples are sodium L-ascorbyl sulfate, potassium L-ascorbyl sulfate, magnesium L-ascorbyl sulfate, calcium L-ascorbyl sulfate and aluminum L-ascorbyl sulfate.

PH Adjusters

The compositions may further comprise a pH adjuster to control the pH of the composition. Particularly, the pH of the composition of the present disclosure is within the range of from about 5 to about 8, or from about 5.2 to about 7.8, or from about 5.4 to about 7.6, for example about 5.4, about 5.6, about 5.8, about 6.0, about 6.2, about 6.4, about 6.6, about 6.8, about 7.0, about 7.2, about 7.4, about 7.6 and any ranges therebetween.

The compositions may further comprise from about 0.01% to about 5%, or from about 0.1% to about 3%, or from about 0.3% to about 2%, or from about 0.4% to about 1.8%, and or from about 0.5% to about 1.6%, for example about 0.4%, about 0.5%, about 0.6%, about 0.7%, about 0.8%, about 0.9%, about 1.0%, about 1.1%, about 1.2%, about 1.3%, about 1.4%, about 1.5%, about 1.6% and any ranges therebetween, by weight of the composition, of a pH adjuster, wherein said pH adjuster is selected from the group consisting of potassium hydroxide, sodium hydroxide, ammonium hydroxide, aminomethyl propanol, triethanolamine, tetrahydroxypropyl ethylene diamine and any combinations thereof.

When a polymeric emulsifier and a pH adjuster is used, it may be desired to optimize the ratio of the polymeric emulsifier to the pH adjuster. For example, the weight ratio of the polymeric emulsifier to the pH adjuster may be between about 1:5 and about 1:0.5, or between about 1:3 to about 1:1, for example about 1:3, about 1:2.5, about 1:2, about 1:1.5, about 1:1.1 and any ranges therebetween.

Thickeners

The compositions may further comprise a thickener (also called a thickening agent) or an additional thickener if the emulsifier in the composition also functions as a thickener. The compositions may comprise from about 0.1% to about 5%, or, alternatively, from about 0.2% to about 2%, of a thickener or an additional thickener when present. Suitable classes of thickeners include but are not limited to carboxylic acid polymers, polyacrylamide polymers, sulfonated polymers, copolymers thereof, hydrophobically modified derivatives thereof, and mixtures thereof.

The thickener may be an acrylate cross linked silicone copolymer network (also sometimes referred to as "polyacrylate siloxane copolymer network"). Suitable thickening agents may also generally include carboxylic acid polymers, polyacrylamide polymers or copolymers, sulfonated polymers, gum, clays, cellulose or modified cellulosic compositions, and the like.

Other Components

In addition to the above described components, the compositions herein may further include preservatives and preservative enhancers such as water-soluble or solubilizable preservatives including Germall 115, methyl, ethyl, propyl and butyl esters of hydroxybenzoic acid, benzyl alcohol, imidazolidinyl urea, EDTA and its salts, Bronopol (2-bromo-2-nitropropane-1,3-diol) and phenoxypropanol; antifoaming agents; binders; biological additives; bulking agents; coloring agents; essential oils and solubilizers thereof; other natural extracts; compounds which stimulate collagen production; yeast fermentation filtrates, and others.

Skin Active Agents

The compositions of the present invention may comprise a skin active agent which provides a particular skin care benefit characteristic of the usage of the skin care product. Herein, skin care benefit may include benefits related to appearance or make-up of the skin. The skin care active can provide acute (immediate and short lived) benefits, or chronic (long term and longer lasting) benefits.

The skin active agents useful herein include skin lightening agents, anti-acne agents, emollients, non-steroidal anti-inflammatory agents, topical anesthetics, artificial tanning agents, anti-microbial and anti-fungal actives, skin soothing agents, sun screening agents such as lotions or creams with SPF, skin barrier repair agents, anti-wrinkle agents, anti-skin atrophy actives, lipids, sebum inhibitors, sebum inhibitors, skin sensates, protease inhibitors, anti-itch agents, hair growth inhibitors, desquamation enzyme enhancers, anti-glycation agents, and mixtures thereof. When included, the present composition comprises from about 0.001% to about 20%, preferably from about 0.1% to about 10% of at least one skin active agent.

The type and amount of skin active agents are selected so that the inclusion of a specific agent does not affect the stability of the composition. For example, hydrophilic agents may be incorporated in an amount soluble in the aqueous phase, while lipophilic agents may be incorporated in an amount soluble in the oil phase.

Other skin active agents purported to exhibit expression-line relaxing benefits for use in the present invention include, but are not limited to, Lavandox available from Barnet Products Corporation; Thallasine 2, available from BiotechMarine; Argireline NP, available from Lipotec; Gatuline In-Tense and Gatuline Expression, available from Gattefosse; Myoxinol LS 9736 from BASF Chemical Company, Syn-ake, available from DSM Nutritional Products, Inc.; and Instensyl®, available from Silab, Inc; Sesaflash™, available from Seppic Inc.

Skin lightening agents useful herein refer to active ingredients that improve hyperpigmentation as compared to pretreatment. Useful skin lightening agents herein include ascorbic acid compounds, vitamin B3 compounds, azelaic acid, butyl hydroxyanisole, gallic acid and its derivatives, glycyrrhizinic acid, hydroquinone, kojic acid, arbutin, mulberry extract, and mixtures thereof. Use of combinations of skin lightening agents is believed to be advantageous in that they may provide skin lightening benefit through different mechanisms.

Ascorbic acid compounds useful herein include ascorbic acid per se in the L-form, ascorbic acid salt, and derivatives thereof. Ascorbic acid salts useful herein include, sodium, potassium, lithium, calcium, magnesium, barium, ammonium and protamine salts. Ascorbic acid derivatives useful herein include, for example, esters of ascorbic acid, and ester salts of ascorbic acid. Particularly preferred ascorbic acid compounds include 2-O-D-glucopyranosyl-L-ascorbic acid, which is an ester of ascorbic acid and glucose and usually referred to as L-ascorbic acid 2-glucoside or ascorbyl glucoside, and its metal salts, and L-ascorbic acid phosphate ester salts such as sodium ascorbyl phosphate, potassium ascorbyl phosphate, magnesium ascorbyl phosphate, and calcium ascorbyl phosphate. Commercially available ascorbic compounds include magnesium ascorbyl phosphate available from Showa Denko, 2-O-D-glucopyranosyl-L-ascorbic acid available from Hayashibara and sodium L-ascorbyl phosphate with tradename STAY C available from Roche.

Vitamin B3 compounds useful herein include, for example, those having the formula:

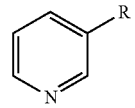

wherein R is —$CONH_2$ (e.g., niacinamide) or —$CH_2OH$ (e.g., nicotinyl alcohol); derivatives thereof; and salts thereof. Exemplary derivatives of the foregoing vitamin B3 compounds include nicotinic acid esters, including non-vasodilating esters of nicotinic acid, nicotinyl amino acids, nicotinyl alcohol esters of carboxylic acids, nicotinic acid N-oxide and niacinamide N-oxide. Preferred vitamin B3 compounds are niacinamide and tocopherol nicotinate, and more preferred is niacinamide. In a preferred embodiment, the vitamin B3 compound contains a limited amount of the salt form and is more preferably substantially free of salts of a vitamin B3 compound. Preferably the vitamin B3 compound contains less than about 50% of such salt and is more preferably essentially free of the salt form. Commercially available vitamin B3 compounds that are highly useful herein include niacinamide USP available from Reilly.

Other hydrophobic skin lightening agents useful herein include ascorbic acid derivatives such as ascorbyl tetraisopalmitate (for example, VC-IP available from Nikko Chemical), ascorbyl palmitate (for example available from Roche Vitamins), ascorbyl dipalmitate (for example, NIKKOL CP available from Nikko Chemical); undecylenoyl phenyl alanine (for example, SEPIWHITE MSH available from Seppic); octadecenedioic acid (for example, ARLATONE DIOIC DCA available from Uniquema); Oenothera biennis seed extract, and pyrus malus (apple) fruit extract, water and Myritol 318 and butylene glycol and tocopherol and ascorbyl tetraisopalmitate and Paraben and Carbopol 980 and DNA/SMARTVECTOR UV available from COLETICA, magnesium ascorbyl phosphate in hyaluronic filling sphere available from COLETICA, and mixtures thereof.

Other skin active agents useful herein include those selected from the group consisting of N-acetyl-D-glucosamine, panthenol (e.g., DL panthenol available from Alps Pharmaceutical Inc.), tocopheryl nicotinate, benzoyl peroxide, 3-hydroxy benzoic acid, flavonoids (e.g., flavanone, chalcone), farnesol, phytantriol, glycolic acid, lactic acid, 4-hydroxy benzoic acid, acetyl salicylic acid, 2-hydroxybutanoic acid, 2-hydroxypentanoic acid, 2-hydroxyhexanoic acid, cis-retinoic acid, trans-retinoic acid, retinol, retinyl esters (e.g., retinyl propionate), phytic acid, N-acetyl-L-cysteine, lipoic acid, tocopherol and its esters (e.g., tocopheryl acetate: DL-α-tocopheryl acetate available from Eisai), azelaic acid, arachidonic acid, tetracycline, ibuprofen, naproxen, ketoprofen, hydrocortisone, acetaminophen, resorcinol, phenoxyethanol, phenoxypropanol, phenoxyisopropanol, 2,4,4'-trichloro-2'-hydroxy diphenyl ether, 3,4,4'-trichlorocarbanilide, octopirox, lidocaine hydrochloride, clotrimazole, miconazole, ketoconazole, neomycin sulfate, theophylline, and mixtures thereof. In a preferred example, the content level of a skin active agent is from about 0.001% to about 20%, more preferably from about 0.1% to about 10%.

Use of the Cosmetic Composition

Various methods of treatment, application, regulation, or improvement may utilize the aforementioned compositions. Application of the present compositions can occur on any skin surface of the body. Skin surfaces of the most concern tend to be those not typically covered by clothing such as facial skin surfaces, hand and arm skin surfaces, foot and leg skin surfaces, and neck and chest skin surfaces (e.g., décolletage). In particular, application may be on a facial skin surface including the forehead, perioral, chin, periorbital, nose, and/or cheek skin surfaces.

Many regimens exist for the application of the composition to the skin. The composition may be applied at least once a day, twice a day, or on a more frequent daily basis, during a treatment period. When applied twice daily, the first and second applications are separated by at least 1 to about 12 hours. Typically, the composition may be applied in the morning and/or in the evening.

The cosmetic composition may be applied as a treatment regimen that includes other products or formulations. A different composition or a secondary application of a different condition such as temperature, penetration enhancers by, devices or ingredients may be applied prior to or following the application of the composition. Preferably, such applications may be incorporated as a second, third, fourth or further treatment steps. Such applications may condition the skin in advance to the treatment application using the cosmetic composition. Any number of products or treatment steps may be included as part of the regimen, in any necessary order. Examples of the uses of the second or different composition includes altering pH, ionic strength, temperature, addition or removal of chemical or biochemical triggers, etc., in advance of the treatment.

The step of applying the composition to the skin may be done by localized application to an area. In reference to application of the composition, the term "localized", "local", or "locally" mean that the composition is delivered the targeted area (such as an area of skin containing wrinkles) while minimizing delivery to skin surface or subdermal layers not requiring treatment. The composition may be applied and lightly massaged into the skin. It is recognized that localized application allows for a reasonable amount of the composition to be applied to areas adjacent the targeted area to be treated (i.e., the composition is unlikely to be applied or to remain within the boundary of the wrinkles without some spreading). The form of the composition or the acceptable carrier should be selected to facilitate localized application. While certain embodiments of the present invention contemplate applying a composition locally to a targeted area, it will be appreciated that compositions of the present invention can be applied more generally or broadly to one or more facial skin surfaces to reduce the appearance of wrinkles within those facial skin regions. Likewise, the compositions can be applied as a continuous film, or in patterns. Striations, patterned spots or random application of the compositions may be desirable. Applicators, as described below, may be beneficial assisting in patterned deposition.

According to a particular method, the compositions may be applied to skin regions where a desired effect is desired. For example, the composition may be applied to the hairline, temples, jawline, and other peripheral facial regions in order to apply an effect to other facial regions. This method utilizes an effect at the periphery of the face to reduce the appearance of wrinkles at, for example, the eye region, smile lines around the mouth, under-eye wrinkles, and to smooth wrinkles around cheek areas. According to this method, the composition may be applied to the periphery of the face without applying the composition directly to targeted areas.

In another aspect, the present disclosure provides a method of improving mammalian skin comprising administering an effective amount of a composition. In some embodiments, the improving of mammalian skin comprises treatment of a mammalian keratinous tissue condition. Such treatment of keratinous tissue conditions can include topical application, including improving the cosmetic appearance of the mammalian keratinous tissue. In some embodiments, the method includes, but is not limited to, preventing, retarding, and/or treating uneven skin tone; reducing the size of pores in mammalian skin; regulating oily/shiny appearance of mammalian skin; thickening keratinous tissue (i.e., building the epidermis and/or dermis and/or subcutis layers of the skin and where applicable the keratinous layers of the nail and hair shaft); preventing, retarding, and/or treating uneven skin tone by acting as a lightening agent or a pigmentation reduction cosmetic agent; preventing, retarding, and/or treating atrophy of mammalian skin; softening and/or smoothing lips, hair and nails of a mammal; preventing, retarding, and/or treating itch of mammalian skin; preventing, retarding, and/or treating the appearance of dark under-eye circles and/or puffy eyes; preventing, retarding, and/or treating sallowness of mammalian skin; preventing, retarding, and/or treating sagging (i.e., glycation) of mammalian skin; preventing and/or retarding tanning of mammalian skin; desquamating, exfoliating, and/or increasing turnover in mammalian skin; preventing, retarding, and/or treating hyperpigmentation such as post-inflammatory hyperpigmentation; preventing, retarding, and/or treating the appearance of spider vessels and/or red blotches on mammalian skin; preventing, retarding, and/or treating fine lines and wrinkles of mammalian skin; preventing, retarding, and/or treating skin dryness (i.e., roughness, scaling, flaking); and preventing, retarding, and/or treating the appearance of cellulite in mammalian skin. In some embodiments, the composition is used to treat the signs of aging. For example, in some embodiments, the composition is used to regulate the signs of aging. In some embodiments, the composition is used to reduce or decrease the signs of aging. In some embodiments, the composition is used to prevent the signs of aging in keratinous tissue (e.g., skin, hair, or nails). Improving keratinous tissue conditions can involve topically applying to the keratinous tissue a safe and effective amount of a composition of the present disclosure.

Non-limiting examples of skin care compositions include, but are not limited to, sunscreens and blocks, mousse, bath and shower gels, lip balms, skin conditioners, cold creams, moisturizers, soaps, body scrubs, body wash, face wash, body spray, exfoliants, astringents, scruffing lotion, depilatories shaving, pre-shaving and after-shaving products, deodorants and antiperspirants, cleansers, skin gels, and rinses, skin lightening and self-tanning compositions. Non-limiting examples of hair care compositions include, but are not limited to, shampoo, conditioner, treatment, styling, hair spray, permanent styling, tonics, cream rinse, hair dye, hair coloring, hair bleaching, hair shine, hair serum, anti-frizz, volumizers, split-end repair, anti-dandruff formulations, and mascara. Non-limiting examples of other cosmetic compositions include but are not limited to make up, including lipstick, rouge, foundation, blush, eyeliner, lip liner, lip gloss, facial or body powder, nail polish, eye shadow, among others. Furthermore, the composition can be applied topically through the use of a patch or other delivery device. Delivery devices can include, but are not limited to, those that can be heated or cooled, as well as those that utilize iontophoresis or ultrasound. In some embodiments, for example, the composition described herein is in the form of a skin lotion, clear lotion, milky lotion, cream, gel, foam, ointment, paste, emulsion, spray, conditioner, tonic, cosmetic, lipstick, foundation, nail polish, after-shave, or the like, which is intended to be left on the skin or other keratinous tissue for some aesthetic, prophylactic, therapeutic or other benefit (i.e., a "leave-on" composition or skin care composition). After applying the composition to the keratinous tissue (e.g., skin), it is preferably left on for a period of at least about 2 minutes, 5 minutes, 15 minutes, more preferably at least about 30 minutes, even more preferably at least about 1 hour, even more preferably for at least several hours, e.g., up to about 12 hours. Any part of the external portion of the face, hair, and/or nails can be treated, (e.g., face, lips, under-eye area, eyelids, scalp, neck, torso, arms, hands, legs, feet, fingernails, toenails, scalp hair, eyelashes, eyebrows, etc.). The application of the present compositions may be done using the palms of the hands and/or fingers or a device or implement (e.g., a cotton ball, swab, pad, applicator pen, spray applicator, etc.).

Another approach to ensure a continuous exposure of the keratinous tissue to at least a minimum level of the composition is to apply the compound by use of a patch applied, e.g., to the face. Such an approach is particularly useful for problem skin areas needing more intensive treatment (e.g., facial crows-feet area, frown lines, under-eye area, upper lip, and the like). The patch can be occlusive, semi-occlusive or non-occlusive, and can be adhesive or non-adhesive. The composition can be contained within the patch or be applied to the skin prior to application of the patch. The patch can also include additional actives such as chemical initiators for exothermic reactions. The patch can also contain a source of electrical energy (e.g., a battery) to, for example, increase delivery of the composition and active agents (e.g., iontophoresis). The patch is preferably left on the keratinous tissue for a period of at least about 5 minutes, or at least about 15 minutes, or at least about 30 minutes, or at least about 1 hour, or at night as a form of night therapy.

Applicators

In some embodiments, the composition may be delivered by a variety of applicators appropriate for localized and general application. By way of example, a suitable applicator may be a dropper and bottle that contains the composition. A pen-like wand with a housing that may contain the composition can also be used. The wand may comprise a handle, a stem, and an applicator head. The applicator head may comprise fibers, foam, cotton, a roller ball or any other suitable material that may releasably hold the composition. Exemplary applicators include devices, penetration enhancers, microneedles, among others.

A simple cotton swab can apply the composition locally to the wrinkled area. The applicator may be configured to easily apply the composition to wrinkled areas having an approximate diameter between about 2 mm and about 20 mm and allowing for a dosed amount of the composition of between about 0.01 to about 2 $mg/cm^2$ or between about 0.1 to about 1 $mg/cm^2$. Thickness of the applied film can be measured or calculated based on the application area and application dose given directly above.

In another embodiment, the applicator may be in the form of a pretreated tape. The tape may be treated or impregnated with the composition herein, then applied to skin via any suitable tape-dispensing mechanism. Therefore, the applicator may take the form of a transdermal patch, a microneedle applicator, or the like.

Kits

As described generally above and herein, the present invention also provides kits comprising the composition thereof. Kits are typically provided in a suitable container (e.g., for example, a foil, plastic, or cardboard package). An inventive kit may include one or more excipients, additives, and the like, as is described herein. The inventive kit may include means for proper administration including an applicator. The inventive kit may include instructions for proper administration and/or preparation for proper administration.

While some methods described herein contemplate applying the compositions of the present invention with an applicator, it will be appreciated that applicators are not required, and the compositions of the present invention can also be applied directly by using one's finger or in other conventional manners.

The dimensions and values disclosed herein are not to be understood as being strictly limited to the exact numerical values recited. Instead, unless otherwise specified, each such dimension is intended to mean both the recited value and a functionally equivalent range surrounding that value.

EXAMPLES

Example 1

Process of Making Aloe Ferment with Structured Water in Fermentation Mixture (Sample 1)

Described below is the process in controlled optimal conditions. A fermentation mixture was made by mixing 1% Aloe Barbadiensis Leaf powder, Q.S. structured water (I/S), and 0.1% *lactobacillus* SP. The fermentation was allowed to process under 25° C. for three days, allowing for the microorganism to grow under optimal conditions. On day 4, the temperature was increased to 45° C. and the conditions were controlled for 24 hours. On day 5, the material was sterilized and filtered. Depending on the batches, the yield of the fermentation (final ferment filtrate versus initial fermentation mixture, w/w) could be from 95% to 99%. The Aloe Barbadensis Leaf Polysaccharides in structured water at 0.03% (w/w) was then added to bring the ferment filtrate back to the initial fermentation mixture weight. Therefore, depending on batches, the Aloe Barbadensis Leaf Polysaccharides (0.03% w/w) solution in structured water was added into the ferment filtration at the amount ranging from about 1% to about 5% of the initial fermentation mixture. When multiple batches were combined together, the combined addition of the Aloe Barbadensis Leaf Polysaccharides (0.03% w/w) solution in structured water were at about 3%

(w/w) of the combined weight of the initial fermentation mixture. The filtration step includes the initial filtration that eliminates the bulk and large particles from the ferment, followed by a multi-filter step where the ferment achieves the appropriate pore size in an incremental down-pore size. The first filter is a D/E filter. After that, the material is placed through a sequential filtration system of 1.0 micron, 0.45 micron, and then a 0.2 micron. The material is then preserved, and finally passed through a sterility filter that is 0.22 micron. The filtration step generally takes anywhere between days to weeks, depending on the bulk material.

Example 2

Comparison Samples (Sample 2, 3, and 4)

Aloe ferment without structured water in fermentation mixture (Sample 2) was made as following: a fermentation mixture was made by mixing 1% Aloe Barbadiensis Leaf powder, Q.S. water, and 0.1% *lactobacillus* SP. The fermentation was allowed to process under 25° C. for three days, allowing for the microorganism to grow under optimal conditions. On day 4, the temperature was increased to 45° C. and the conditions were controlled for 24 hours. On day 5, the material was sterilized and filtered. Depending on the batches, the yield of the fermentation (final ferment filtrate versus initial fermentation mixture, w/w) could be from 95% to 99%. The Aloe Barbadensis Leaf Polysaccharides in structured water at 0.03% (w/w) was then added to bring the ferment filtrate back to the initial fermentation mixture weight. Therefore, depending on batches, the Aloe Barbadensis Leaf Polysaccharides (0.03% w/w) solution in structured water was added into the ferment filtration at the amount ranging from about 1% to about 5% of the initial fermentation mixture. When multiple batches were combined together, the combined addition of the Aloe Barbadensis Leaf Polysaccharides (0.03% w/w) solution in structured water were at about 3% (w/w) of the combined weight of the initial fermentation mixture. The filtration step includes the initial filtration that eliminates the bulk and large particles from the ferment, followed by a multi-filter step where the ferment achieves the appropriate pore size in an incremental down-pore size. The first filter is a D/E filter. After that, the material is placed through a sequential filtration system of 1.0 micron, 0.45 micron, and then a 0.2 micron. The material is then preserved, and finally passed through a sterility filter that is 0.22 micron. The filtration step generally takes anywhere between days to weeks, depending on the bulk material.

*Lactobacillus* ferment without structured water or Aloe in fermentation mixture (Sample 3) was made as following: a fermentation mixture was made by mixing 1% glucose, Q.S. water, and 0.1% *lactobacillus* SP. The fermentation was allowed to process under 25° C. for three days, allowing for the microorganism to grow under optimal conditions. On day 4, the temperature was increased to 45° C. and the conditions were controlled for 24 hours. On day 5, the material was sterilized and filtered. The filtration step includes the initial filtration that eliminates the bulk and large particles from the ferment, followed by a multi-filter step where the ferment achieves the appropriate pore size in an incremental down-pore size. The first filter is a D/E filter. After that, the material is placed through a sequential filtration system of 1.0 micron, 0.45 micron, and then a 0.2 micron. The material is then preserved, and finally passed through a sterility filter that is 0.22 micron. The filtration step generally takes anywhere between days to weeks, depending on the bulk material.

Aloe Barbadensis Leaf Polysaccharides (Sample 4) was purchased from Ashland under the tradename of ALOE VERA IL SD PWD 200X 705AV ORGANIC.

Example 3

Efficacy Study Comparison (Samples 1, 2, 3, and 4)

Each of the samples 1, 2, 3, and 4 was made as 2% solution in the purified water, and mixed by vortexing and/or sonicating if needed. Each sample was assayed by using a modified protocol of the Randox TAS Kit:

In a 96-well plate, reagents and samples were added to each well that is being assayed (n=3). Maximum of 36 wells can be used due to instrument limitations. Absorbance (600 nm) is measured in a Spectramax Plate Reader over a period of 2 minutes in order to determine antioxidant capacity. Rates are calculated, and then inhibition of oxidation as compared to the water blank for each sample was calculated. BHT was tested at 0.001% as a control, and is in range of what is expected.

TABLE 1

In Vitro antioxidant activity testing (Randox TAS) results of Sample 1, 2, 3, and 4 compared to water blank.

|  | BHT | Sample 1 | Sample 2 | Sample 3 | Sample 4 |
| --- | --- | --- | --- | --- | --- |
| Antioxidant Activity Increase (%) | 31.4 | 25.5 | 3.0 | 7.5 | 3.2 |
| se | 2.9 | 5.1 | 0.8 | 0.2 | 0.2 |

Thus, the experimental results in Table 1 clearly showed that Sample 1 (structured water used as fermentation medium) was significantly better at inhibiting oxidation than Samples 2 (almost the same production process as Sample 1 except that no structured water was used in fermentation medium in Sample 2), 3, and 4 when tested in this assay at the same concentration.

Example 4

The Stimulating Activity Of The Aloe Ferment In Adult Normal Human Dermal Fibroblasts (NHDF)

Aloe Ferment (Sample 1) was tested for collagen enhancing activity in an ELISA assay. Aloe Ferment was found to increase collagen synthesis in a dose dependent manner. Collagen synthesis was increased by 16%, 21%, and 48% at 0.25%, 0.5%, and 1% (v/v), respectively. In the assay, 20 ng/ml of TGFβ was found to increase collagen synthesis by 91%.

Adult NHDF cells from Clonetics were seeded and grown to confluence in a 96 well plate (Corning/Costar flat bottom) prior to being treated. The samples were tested with Aloe Ferment at 0.125%, 0.25%, 0.5% and 1% (v/v). The plate was incubated for 3 days at 37° C./5% $CO_2$ before the supernatants were harvested and stored at −80° C. in siliconized tubes until the ELISA was performed. The PIP ELISA was performed, and the results were calculated from the standard curve. For the pro-collagen ELISA the supernatants were diluted 1:200. In the assay, TGFβ (20 ng/ml) was run as a positive control. The cell viability was determined via a standard MTT assay. The statistical significance was performed using one-way ANOVA followed by Dunnett's post-hoc test. All results have p<0.01. All analyses were performed using GraphPad Instat.

TABLE 2

The ELISA assay results on enhanced collagen production in vitro using the Aloe ferment (Sample 1).

|  | TGFB | 0.125% | 0.25% | 0.5% | 1.0% |
|---|---|---|---|---|---|
| Collagen Synthesis Change (%) | 91 | −9 | 16 | 21 | 48 |

The Table 2 shows the results of the Aloe Ferment when tested at 0.125%, 0.25%, 0.5% and 1% (v/v) for collagen enhancing activity. Collagen synthesis was significantly changed by −9%, +16%, +21% and +48%, respectively while cell viability was not significantly affected. The results conclude that Aloe Ferment enhanced collagen synthesis at 0.25%, 0.5%, and 1% in a dose dependent manner.

Example 5

Clinical Moisturization Study

Two clinical studies were conducted to study the effect of the composition comprising the aloe ferment (Sample 1) according to the present invention described herein. Particularly, the moisturization effect of the composition on the human skin was studied.

Study participants (N=16 and N=110) were enrolled in the respective studies. The study participants included all age groups between 19 y/o to 65 y/o and all skin types including, dry, oily and combination skin. The participants applied the composition on the clean skin during the day both, morning and evening. The composition was massaged topically on the clean skin and the study protocol did not introduce any other skin care product during the study period. The moisturization effect on the participant's skin were measured. All participants (100%) showed immediate improvement and moisturization upon topical application of the composition. About 89% of participants showed improved moisturization at 72 hours following the topical application. About 68% of participants showed improved moisturization at 100 hours following the topical application.

Example 6

Study on the Effect of the Aloe Ferment on Melanoderm, In Vitro

An in vitro study was performed to evaluate the effect of the aloe ferment (Sample 1) according to the present invention described herein on melanoderms. Particularly, the skin lightening and skin brightening effect was studied.

The aloe ferment/extract was diluted to 1% (v/v) in DPBS and then further diluted to 0.5% to 0.125% in DPBS. The solutions were prepared prior to the study treatment. Study sample, i.e., tissues were treated daily (except weekends) with 3 μl of the diluted aloe ferment for 14 days. The volume of the solution was pipetted so that the amount left on the insert was 2 μl after application with the tip of a sterile glass rod. Prior to the application, the inserts were washed by DPBS twice. Viability of the tissues and the amount of melanin were measured after 7 and 14 days of treatment.

Melanin Analysis: Tissues were removed from the plastic insert and placed in 250 μl Solvable in a 0.6 mL microfuge tube. Tissues were incubated overnight at 60° C. Samples were vortexed and then centrifuged at 13,000 rpm for 5 minutes. 200 μl of the samples were pipetted into a 96-well plate, read at 490 nm on the spectrophotometer and measured against melanin standards.

TABLE 3

The in vitro effect (melanin) of the aloe ferment on melanoderm tissues.

| | Aloe ferment (Sample 1) concentration | | | |
|---|---|---|---|---|
| | 0.125% | 0.25% | 0.5% | 1.0% |
| Change compared to untreated (%, 7 days) | 20.23 | 7.58 | −6.66 | −13.65 |
| Change compared to untreated (%, 14 days) | 5.98 | −17.88 | −18.81 | −22.18 |

Viability Analysis: A 10% alamar blue solution was made by combining 13 mL alamar blue with 117 mL maintenance media. The maintenance media was removed from each well and replaced with 5 mL of 10% alamar blue in each well. The inserts were incubated in 10% alamar blue for 2 hours. The fluorescence of each well was measured on the Spectra Max M2$^e$ plate reader at 530 nm excitation and 590 nm emission after the removal of the inserts.

TABLE 4

The in vitro effect (viability) of the aloe ferment (Sample 1) on melanoderm tissues.

| | Aloe ferment (Sample 1) concentration | | | |
|---|---|---|---|---|
| | 0.125% | 0.25% | 0.5% | 1.0% |
| Change compared to untreated (%, 7 days) | −17.45 | −19.86 | 15.11 | 6.26 |
| Change compared to untreated (%, 14 days) | −11.68 | −23.87 | 0.49 | 23.37 |

The study results shown in Table 3 and 4 indicates that in one week, the 1% aloe ferment was effective in reducing normalized melanin by 14%, while increasing viability of the tissues by 6%. In two weeks, the 1% aloe ferment was effective in reducing melanin by 22%, while increasing viability by 23%. Further, the 0.25% and 0.5% aloe ferment were also effective in reducing melanin by 18% and 19%, respectively.

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the scope of the invention. It is therefore intended to cover in the appended claims all such changes and modifications that are within the scope of this invention.

What is claimed is:

1. A cosmetic composition comprising a ferment, the ferment comprising:
    a structured water solution or suspension comprising at least one cosmetic active ingredient comprising Aloe barbadensis leaf polysaccharides and a first structured water component; and
    a fermentation product,
    wherein the fermentation product is produced by fermenting a fermentation mixture comprising:
        at least one probiotic microorganism, wherein the at least one probiotic microorganism comprises a strain from *Lactobacillus* genus;
        at least one prebiotic active ingredient comprising Aloe barbadensis leaf powder; and
        a second structured water component,
    wherein the fermentation product is a sterile filtrate,
    wherein the first and second structured water components contain stabilized clusters of ions and comprise I water and S water,
    wherein the I water has a conductivity of between 500 μS/cm and 3000 μS/cm and a pH of between 2.0 and 3.0,
    wherein the S water has a conductivity of between 600 μS/cm and 2500 μS/cm and a pH of between 10.0 and 12.0, and
    wherein each of the I water and S water is produced from starting water with a conductivity of between 250 μS/cm and 450 μS/cm and a pH of between 7.0 and 7.5.

2. The cosmetic composition of claim 1, wherein the at least one cosmetic active ingredient further comprises hyaluronic acid.

3. The cosmetic composition of claim 1, wherein the ferment comprises I water in an amount of from 1% to 60% by weight of the ferment.

4. The cosmetic composition of claim 1, wherein the ferment comprises S water in an amount of from 1% to 60% by weight of the ferment.

5. The cosmetic composition of claim 1, wherein the at least one prebiotic active ingredient further comprises aronia berry, raspberry, spinach, cherry broccoli, tart cherry, apple, mushroom, grape juice, beet, blueberry, blackberry, acai, coffee, ginger, cranberry, aloe gel, coconut water, pomegranate, mango, apricot, retinol, lavender, honey, cardamom, truffle, hyaluronic acid or mixtures thereof.

6. The cosmetic composition of claim 5, wherein the at least one prebiotic active ingredient further comprises hyaluronic acid.

7. The cosmetic composition of claim 1, wherein the strain from *Lactobacillus* genus is selected from the group consisting of *Lactobacillus johnsonii, Lactobacillus paracasei, Lactobacillus acidophilus, Lactobacillus amylovorus, Lactobacillus casei, Lactobacillus rhamnosus, Lactobacillus brevis, Lactobacillus crispatus, Lactobacillus delbrueckii, Lactobacillus fermentum, Lactobacillus helveticus, Lactobacillus gallinarum, Lactobacillus gasseri, Lactobacillus plantarum, Lactobacillus reuteri, Lactobacillus salivarius, Lactobacillus alimentarius, Lactobacillus curvatus, Lactobacillus sake*, and mixtures thereof.

8. The cosmetic composition of claim 1, wherein the structured water solution or suspension comprises the at least one cosmetic active ingredient in an amount within a range of from 0.0001% to 20% by weight relative to a total weight of the structured water solution or suspension.

9. The cosmetic composition of claim 1, wherein the cosmetic composition comprises the ferment in an amount of from 0.00001% to 20% by weight, relative to a total weight of the cosmetic composition.

10. The cosmetic composition of claim 1, wherein the ferment comprises the structured water component in an amount of from 1% to 99.5% by weight, relative to the total weight of the ferment.

11. The cosmetic composition of claim 1, wherein the fermentation mixture comprises the at least one prebiotic active ingredient in an amount ranging from 0.001% to 20% by weight, relative to the total weight of the fermentation mixture.

12. The cosmetic composition according to claim 1, wherein the composition is a skin lotion, skin softener, skin toner, astringent, lotion, milk lotion, moisturizing lotion, nutrition lotion, massage cream, facial mask, facial cleanser, nutrition cream, moisturizing cream, hand cream, foundation, primer, essence, nutrition essence, cleansing foam, cleansing lotion, cleansing cream, body lotion, cream with sun protection factor (SPF), lotion with SPF, body mask, or body cleanser.

13. The cosmetic composition of claim 1, wherein the structured water solution or suspension comprises the at least one cosmetic active ingredient in an amount ranging from 0.01% to 0.1% by weight relative to a total weight of the structured water solution or suspension.

14. The cosmetic composition of claim 1, wherein the ferment comprises the structured water solution or suspension in an amount of from 1% to 5% by weight relative to a total starting weight of the fermentation mixture.

15. The cosmetic composition of claim 1, comprising:
    the structured water solution, wherein the structured water solution comprises Aloe barbadensis leaf polysaccharides at an amount of 0.03% by weight relative to a total weight of the structured water solution,
    wherein the fermentation mixture comprises the strain from *Lactobacillus* genus at an amount of 0.1% by weight relative to an initial weight of the fermentation mixture,
    wherein the fermentation mixture comprises the Aloe barbadensis leaf powder at an amount of 1% by weight relative to the initial weight of the fermentation mixture,
    wherein the ferment comprises the structured water solution at an amount within a range of from 1% to 5% by weight relative to the initial weight of the fermentation mixture.

16. A method of increasing collagen production in human skin, the method comprising applying a cosmetic composition comprising a ferment to the human skin, the ferment comprising:
    a structured water solution or suspension comprising at least one cosmetic active ingredient comprising Aloe barbadensis leaf polysaccharides and a first structured water component; and
    a fermentation product,
    wherein the fermentation product is produced by fermenting a fermentation mixture comprising:
        at least one probiotic microorganism, wherein the at least one probiotic microorganism comprises a strain from *Lactobacillus* genus;
        at least one prebiotic active ingredient comprising Aloe barbadensis leaf powder; and
        a second structured water component,
    wherein the fermentation product is a sterile filtrate, wherein the first and second structured water components contain stabilized clusters of ions and comprise I water and S water;

wherein the I water has a conductivity of between 500 µS/cm and 3000 µS/cm and a pH of between 2.0 and 3.0, wherein the S water has a conductivity of between 600 µS/cm and 2500 µS/cm and a pH of between 10.0 and 12.0, and wherein each of the I water and S water is produced from starting water with a conductivity of between 250 µS/cm and 450 µS/cm and a pH of between 7.0 and 7.5.

17. The method of claim 16, wherein applying the cosmetic composition comprises applying the composition once, twice or thrice a day or prior to retiring to bed at night.

18. The method of claim 16, wherein applying the cosmetic composition enhances hydration and moisturization of the skin for up to 100 hours upon topical application.

19. The method of claim 16, wherein applying the composition provides skin brightening and skin lightening effect on the skin upon topical application.

* * * * *